United States Patent [19]

Matsunaga et al.

[11] 4,439,417

[45] Mar. 27, 1984

[54] SHAMPOO COMPOSITION

[75] Inventors: Kinjiro Matsunaga, Miyashiro; Takeo Okumura, Sakura; Sachio Naito, Tokyo; Rikio Tsushima, Wakayama, all of Japan

[73] Assignee: Kao Soap Co., Ltd., Tokyo, Japan

[21] Appl. No.: 316,489

[22] Filed: Oct. 29, 1981

[30] Foreign Application Priority Data

Nov. 14, 1980 [JP]  Japan .................... 55-160357

[51] Int. Cl.³ .................... A61K 7/06; A61K 7/09; A61K 7/11
[52] U.S. Cl. .................... 424/70; 424/DIG. 1; 424/71; 424/72
[58] Field of Search .................... 424/70, DIG. 2, 70, 424/359

[56] References Cited

U.S. PATENT DOCUMENTS

| | | | |
|---|---|---|---|
| 3,033,755 | 5/1962 | Jacobi | 424/59 X |
| 3,806,501 | 4/1974 | Rymer et al. | 260/123.7 |
| 3,904,748 | 9/1975 | Eckert et al. | 424/70 |
| 3,957,065 | 5/1976 | Busch et al. | 424/359 |
| 3,961,634 | 6/1976 | Busch | 132/7 |
| 4,041,150 | 8/1977 | Karjala | 424/72 |
| 4,279,996 | 7/1981 | Yoshioka et al. | 424/72 |

FOREIGN PATENT DOCUMENTS

| | | | |
|---|---|---|---|
| 2940220 | 4/1980 | Fed. Rep. of Germany | 424/71 |
| 2438662 | 6/1983 | France | 424/70 |
| 22643 | of 1907 | United Kingdom | 424/70 |
| 1111934 | 5/1968 | United Kingdom | 424/70 |
| 2061956A | 5/1981 | United Kingdom | 424/70 |

OTHER PUBLICATIONS

*Textile Progress,* vol. 7, No. 1, 1975, pp. 1–70, The Textile Institute, Manchester, (GB); N. H. Leon et al: "The Chemical Reactivity and Modification of Keratin Fibres".

*Primary Examiner*—Dale R. Ore
*Attorney, Agent, or Firm*—Oblon, Fisher, Spivak, McClelland & Maier

[57] ABSTRACT

A shampoo composition is provided which is of the type which comprises a shampoo base containing at least one anionic surface active agent and a decomposition derivative of keratin material. The decomposition derivative is one or more of (1) decomposition products obtained by oxidation of keratin materials and derivatives at a thiol group of decomposition products obtained by reduction of keratin material.

5 Claims, No Drawings

SHAMPOO COMPOSITION

BACKGROUND OF THE INVENTION

1. Field of the Invention

This invention relates to a shampoo composition and more particularly, to a shampoo composition which comprises a shampoo base containing anionic surface active agents and decomposition derivatives of keratin material and which shows an excellent hair conditioning effect and mild eye irritation.

2. Description of the Prior Art

Hitherto employed shampoos generally comprise singly or in combination, as their base, anionic surface active agents such as alkylsulfates and polyoxyethylenealkylsulfates and the like, nonionic surface active agents such as polyoxyethylene alkyl ethers, fatty acid alkylolamides and the like, or amphoteric surface active agents such as alkylbetaines, alkylamine oxides and the like.

On washing of hair with the shampoos containing these bases, it will be found that the sebum or other oils existing on the hair surface are washed off too much, so that the feeling of the washed hair becomes very poor to the touch and hard to comb or brush. In addition, when completely dried, such hair is hard to style. Especially in winter season of low humidity, since static electricity is ready to generate on brushing, there occurs a phenomenon such as of hair fly with the attendant disadvantage that the hair is hard to comb, causing split-ends or broken hairs.

In order to overcome the above disadvantage, there is known a method of adding oils to ordinary shampoo bases to supplement the oil at the time of washing. Ordinarily employed shampoos are admixed with a variety of oils.

However, in the formulation system of shampoo, the system is in an emulsified or solubilized state by the action of surface active agents, so that it is difficult to add oils in amounts sufficient for scalp and hair without impairing the stability of the system.

With shampoos to which large amounts of oil are added, an amount of adsorption of oil on hair increases but they involve disadvantages that lathering and detergency which shampoos should orginally have deteriorate extremely with the commercial value being considerably impaired.

In recent years, on the other hand, there have been proposed many shampoo compositions including cationic polymers for the purpose of imparting a rinsing effect to hair after washing. However, these compositions have the following disadvantaages: (1) Showing a conditioning effect but deteriorated in lathering ability and detergency; (2) Colored or discolored as time goes; (3) Excellent in lathering characteristics but poor in conditioning effect; and (4) High in cost.

SUMMARY OF THE INVENTION

It is an object of the present invention to provide a shampoo composition which can overcome the disadvantages of the known shampoo compositions and has such as consitioning effect as to impart softness and smoothness to hair after washing.

It is another object of the invention to provide a shampoo composition which comprises anionic surface active agents and decomposition derivatives of kertain materials in combination whereby excellent touches such as of softness, smoothness and the like and excellent conditioning effects such as of combing ease can be imparted to pair after washing without sacrifices of properties of the shampoo composition itself.

The above objects can be achieved according to the present invention by a shampoo composition which comprises a shampoo base containing anionic surface active agents and a decomposition derivative of keratin material selected from the group consisting of (1) decomposition products obtained by oxidation of keratin materials, (2) derivatives at the thiol group of decomposition products obtained by reduction of keratin materials and a mixture thereof.

DETAILED DESCRIPTION AND EMBODIMENTS OF THE INVENTION

Preferable anionic active agents to be used as the base of the shampoo composition include:

(1) Linear or branched alkylbenzenesulfonates whose alkyl group has 10-16 carbon atoms on average;

(2) Polyoxyalkylenealkylsulfates added with 0.5-8 moles, in average, of ethylene oxide and/or propylene oxide per molecule, which have a linear or branched alkyl group having 8-20 carbon atoms on average;

(3) Alkylsulfates whose alkyl group has 10-20 atoms on average;

(4) Olefinsulfonates having 10-12 carbon atoms on average in one molecule thereof;

(5) Alkanesulfonates having 10-20 carbon atoms on average in one molecule thereof;

Alkylethoxycarbonates having 10-20 carbon atoms on average in the alkyl group thereof and added with 0.5-8 moles of ethylene oxide on average in one molecule thereof; and (7) Derivatives of succinic acid represented by the formula

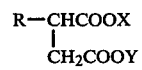

(in which R represents an alkyl group or alkenyl group having 6-20 carbon atoms and X and Y independently represent a counter ion).

The counter ions of these anionic surface active agents include alkali metal ions such as sodium, potassium and the like, alkaline earth metal ions such as calcium, magnesium and the like, ammonium ions, and alkanolamines having 1-3 alkanol groups having 2 or 3 carbon atoms (e.g. monoethanolamine, diethanolamine, triethanolamine, triisopropanolamine and the like).

Preferable anionic surface active agents among those mentioned above are linear or branched alkylsulfates having 10-16 carbon atoms on average, polyoxyethylenealkylsulfates (having an average number of added moles of (0.5-8) whose alkyl group has 8-20 carbon atoms on average, or olefinsulfonates having 10-16 carbon atoms on average, which are used singly or in combinations.

The decomposition derivatives of keratin material to be used in the present invention are (1) decomposition products obtained by oxidation of a keratin material, (2) derivatives at the thiol group of decomposition products obtained by reduction of a keratin which are prepared in the following manner and have an average molecular weight of 30,000-100,000 and a mixture thereof.

The starting keratin materials include, for example, animal hair, human hair, feather, claw, horn, hoof and scale, among which wool, the hairs and feather are preferably used. These keratin materials may be subjected to the oxidation or reduction reaction as they are but, if necessary, may be cut or reduced into pieces of a suitable size or may be pretreated such as by washing and defatting.

(1) Decomposition products obtained by oxidation of keratins The oxidation of keratin is feasible by a variety of methods known per se (N. H. Leon; Textile Progress, Vol. 7, page 1 (1975)). Oxidizing agents are preferably organic or inorganic agents of the type which electrophilically acts on the disulfide bond (S-S bond) in the keratin structure. Examples of the oxidizing agents include organic peracids, inorganic peroxo acids of their salts, permanganic acid or its salts, chromic acid or related compounds, halogens, peroxides, oxyacids or their salts, and the like, among which the organic peracids such as peracetic acid, performic acid and perbenzoic acid are preferable. The oxidation reaction is conducted in liquid media using oxidizing agents in excess with respect to the disulfide bonds in the keratin material, ordinarily in the amounts of over two equivalents or more, preferably 4–10 equivalents, of the disulfide bonds. The reaction is feasible under acidic or alkaline conditions and is preferably conducted under acidic conditions and particularly weakly acidic conditions. The reaction temperature and pressure are varied depending on the types of the oxidizing agent and keratin material and are not critical. Room temperature is generally sufficient but, if necessary, heat may be applied. An atmospheric pressure is satisfactorily used in the practice of the invention but the reaction may be conducted under reduced pressure or under pressure. By this, the disulfide bond of keratin material is cleft into sulfonic acid ($-SO_3H$).

(2) Derivatives at the thiol group of decomposition products obtained by reduction of keratin materials. Reducing agents employed for reducing keratin materials are preferably organic or inorganic reducing agents of the type which serves to cleave the disulfide bond in the keratin structure into a thiol group ($-SH$) and generally acts nucleophilically on the disulfide bond. Examples of the reducing agents include organic reducing agents such as mercaptoethanol, thioglycollic acid, benzylmercaptan, 1,4-dithiothreitol, tributylphosphine and the like, and inorganic reducing agents such as sodium hydrogensulfite, sulfides such as sodium hydrosulfide, metallic hydrides such as lithium aluminium hydride. The amount of the reducing agent is usually in the range of 2–10 equivalents of the disulfide bonds in keratin material. The pH of the reaction system is in the range of 2–12, preferably 6–11. Outside the range, the hydrolysis undesirably takes place at the same time. Room temperature is sufficient for the reaction but heat may be applied to shorten the reaction time. The reaction time is ordinarily in the range of 2–3 hours or more. Since the thiol group produced by the reduction is required not to be substantially oxidized, the reduction operation should conveniently be carried out in an atmosphere of inert gas to give good results. The decomposition product obtained by the reduction of the keratin materials is then chemically modified at the thiol group thereof to obtain a derivative thereof. The derivatives at the thiol group include:

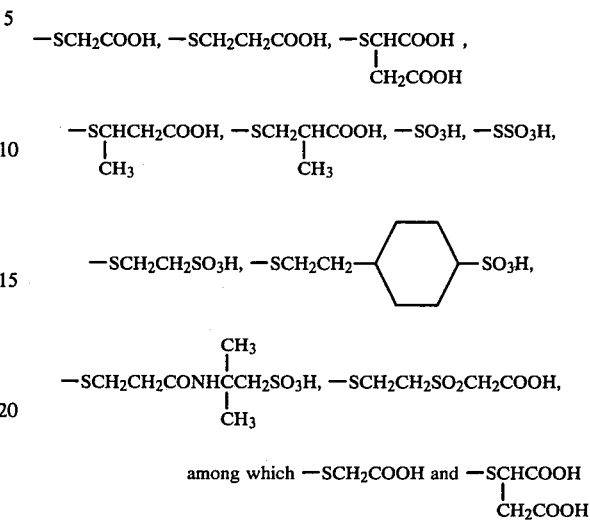

preferable. The chemical modification of the thiol group is known per se and can be conducted, for example, based on the procedures known from N. H. Leon; Textile Progress, Vol. 7, page 1 (1975), "Yuki Ioo Kagobutsu (Organic Sulfur Compounds)" written by Shigeru Ookyo and published by Kagaku Dojin (1968) and "Kobunshi Jikkengaku Koza" written by Masami Oku, Vol. 12, Kyoritsu Shuppan (1957). Typical methods are shown below.

(a) Method utilizing the nucleophilic substitution reaction of SH groups $$K-SH+R-L \quad K-S-R+HL$$

(in which K represents a residue of a keratin compound, R represents a chemically modifying group to be introduced; and L represents a leaving atom or group such as a halogen atom or acid residue). Compounds which react by this method include, for example, halogen compounds such as iodoacetic acid, bromoacetic acid, chloroacetic acid and the like.

(b) Method utilizing the nucleophilic addition reaction of SH group with a double bond between carbon atoms

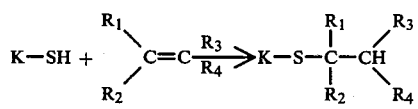

(in which at least one of $R_1$, $R_2$, $R_3$ and $R_4$ represents a carboxyl group or sulfonic acid group, the other represent an alkyl group or hydrogen atom, and K has the same meaning as defined hereinbefore). Compounds which react by this method include, for example, acrylic acid, methacrylic acid, crotonic acid, maleic acid, fumaric acid, vinyl carboxymethylsulfone, vinylsulfonic acid, styrenesulfonic acid, 2-acrylamido-2-methyl-propanesulfonic acid and the like.

(c) Method using a substitution reaction between SH group and sulfite compound

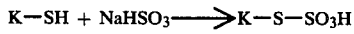

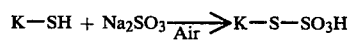

(in which K has the same meaning as defined hereinbefore).

(d) Method of oxidizing SH group into sulfonic acid group

(in which K has the same meaning as defined hereinbefore). The oxidizing agents used in this reaction include, for example, halogens, permanganates and the like.

The decomposition derivatives of the keratin material used in the present invention are originally insoluble in polar solvents such as water, ethanol, propylene glycol and the like but show solubility in the presence of anionic surface active agents. In order to further increase the solubility, it is desirable to use alkaline materials in combination or for forming salts with the derivative. Examples of the alkaline materials include inorganic alkali compounds such as sodium hydroxide, potassium hydroxide and the like and organic alkali compounds such as ammonia, ethanolamine, diethanolamine, triethanolamine, 2-amino-2-methylpropanol, aminomethylmercaptopropanediol, triisopropanolamine, glycine, arginine, histidine and the like.

The shampoo composition according to the invention is prepared by adding 0.05–10 wt% (hereinafter referred to simply as %), preferably 0.2–3%, of one or more of the decomposition derivatives of keratin material to a shampoo base containing 5–30%, preferably 10–25%, of one or more of anionic surface active agents. Less amounts of the decomposition derivative than 0.1% are not favorable since satisfactory effects are not shown, whereas larger amounts than 10% are unfavorable since hair becomes sticky under high humidity conditions.

Preferably, the shampoo composition of the invention is so adjusted that the pH of its 5% aqueous solution is in the range of 4–8.

The shampoo composition of the invention may further comprise, aside from the above-described two essential components, ingredients added to known shampoo compositions. For instance, there may be added, if necessary, the following ingredients in such amounts as not to impair the effect of the invention: amphoteric surface active agents, nonionic surface active agents, cationic surface active agents, solubilizing agents such as propylene glycol, glycerine, urea and the like, viscosity-adjusting agents such as ethyl alcohol, isopropyl alcohol, hydroxyethyl cellulose, methyl cellulose, higher alcohols, and the like perfumes, colorants, UV absorbers, antioxidants, preservatives, pearling agents, and lotioning agents.

The thus obtained shampoo composition of the invention not only is excellent in hair conditioning effect and washing effect, but also shows milder eye irritation than known shampoo compositions when getting in eyes by accident and only a gentle influence on the conjuctiva and iris.

The present invention is particularly described by way of references and examples, which should not be construed as limiting the present invention thereto.

Reference 1

Preparation of oxidation decomposition derivatives of keratin materials:

(a) Ten grams of wool fibers were immersed in 700 g of 8% aqueous peracetic acid solution at room temperature for 1 day for the oxidation reaction. The resulting oxidized wool was filtered and washed with water, and then immersed in 700 g of a 0.1 N ammoniacal solution at room temperature for 1 day, permitting about 90% of the wool to dissolve in the ammoniacal solution. About 1 g of the insoluble matters were removed by filtration and the aqueous ammoniacal solution of keratose as an oxidized decomposition product of wool keratin was admixed with 2 N hydrochloric acid to adjust pH to 4.0 whereupon α-keratose was settled as a precipitate. This precipitate was filtered, washed with acetone and dried to obtain 5.4 g of α-keratose.

(b) Wool fibers were heated under pressure in an autoclave by the use of saturated steam of 6 kg/cm² for 6 minutes and were abruptly released into the air to obtain a porous swollen matter. Ten grams of the swollen matter which had been reduced to pieces, 250 g of formic acid and 50 g of a 30% aqueous hydrogen peroxide solution were charged into a 500 ml three neck distillation flask to immerse the pieces at room temperature for 1 day, whereupon no powder was found in the solution with the foam-like matter being floated on the upper layer. This reaction mixture was filtered and the filtrate was poured into 1.5 liters of water, followed by adding hydrochloric acid to adjust the pH to 4. The resulting precipitate was collected by filtration and washed with 500 ml of water to obtain 4.5 g of α-keratose. To the insoluble matters from which the reaction product had been removed by filtration were added 350 ml of water and then an ammoniacal solution to adjust the pH to 11, and the matters were immersed at room temperature for 1 day. The system was filtered and the filtrate was added with hydrochloric acid to adjust the pH to 4. The resulting precipitate was collected by filtration to obtain 0.7 g of α-keratose. It was found that 1.4 g of the insoluble matters were primarily made of β-keratose.

Reference 2

Preparation of reduced decomposition derivatives of keratin materials:

(a) Ten grams of wool fibers were immersed in 600 ml of an aqueous solution with concentrations of 8 M urea and 0.01 M Tris buffer, to which was added 6 ml of 2-mercaptoethanol, followed by adjusting the pH to 10 by means of a 5 N potassium hydroxide aqueous solution to conduct the reduction reaction in an atmosphere of nitrogen at room temperature. About 3 hours after commencement of the reaction, the wool was allowed to dissolve in the reaction solution in an amount of about 85% thereof. While the system was adjusted with a 5 N potassium hydroxide aqueous solution so as not to permit the pH below 7, 16.5 g of iodoacetic acid was gradually added and the pH of the system was finally adjusted to 8.5 to carry out the carboxymethylation reaction at room temperature for 2 hours. The reaction solution was filtered to remove insoluble matters therefrom and the resultant filtrate was charged into a cellulose tube wherein it was dialyzed against deionized water to remove low molecular weight impurities including urea. As the urea was dialyzed, the content in the cellulose tube was turned white since HGT (component with high contents of glycine and tyrosine) to be a water-insoluble component precipitated. After completion of the dialysis, the HGT was removed by centrifugal separation and S-carboxymethyl kerain (SCMKA) was obtained from the neutral transparent aqueous solution of SCMKA by the isoelectric precipitation method. That is, 1 N hydrochloric acid was added to the system to adjust its pH to 4.4 by which SCMKA was turned insoluble and separated as precipitate. This precipitate was filtered, washed with ethanol and dried to obtain 4.2 g of SCMKA.

(b) The procedure of Reference 2-(a) was repeated except that there were used instead of wool fibers feathers which were heated for 6 minutes in an autoclave by means of superheated steam of 6 kg/cm$^2$ and 240° C. and then abruptly released in the air to obtain a porous swollen matter and that 1.75 g of maleic acid was used instead of iodoacetic acid, thereby obtaining 5.3 g of S-(1,2-dicarboxyethyl)-keratin.

(c) The procedure of Reference 2-(a) was repeated using a powder of hoof of horse instead of wool fibers and 11 g of acrylic acid instead of iodoacetic acid, thereby obtaining 4.2 g of S-(2-carboxyethyl)-keratin.

(b) The procedure of Reference 2-(a) was repeated using 28 g of styrenesulfonic acid instead of iodoacetic acid, thereby obtaining 4.8 g of S-(sulfophenylvinyl)-keratin.

(e) Eight grams of wool fibers were dispersed in 300 ml of n-propanol and 300 ml of a 0.1 N Tris buffer solution. After substitution with nitrogen, 3.2 ml of tri-n-butylphosphine was added, followed by agitaing at room temperature for 24 hours. After the solution was subjected to filtration, to the insoluble matters were addee 400 ml of water, 9.28 g of maleic acid and about 30 ml of 5 N potassium hydroxide to adjust the pH to 8.0, followed by agitating at room temperature for 6 hours. To the reaction system was added about 20 ml of a 28% aqueous ammoniacal solution to adjust the pH to 11.5, after which it was agitated at room temperature for 18 hours. The reaction solution was filtered to remove insoluble portion therefrom and the resultant filtrate was placed in a cellulose tube in which it was dialyzed against deionized water to remove low molecular weight impurities therefrom. After completion of the dialysis, the insoluble matters in the cellulose tube were removed by centrifugal separation and the neutral transparent aqueous solution was adjusted to have a pH of 4.4 by addition of about 5.5 ml of 1 N hydrochloric acid and the resulting precipitate was collected by filtration, followed by washing with ethanol and drying to obtain 3.9 g of S-(1,2-dicarboxyethyl)-keratin.

(f) The procedure of Reference 2-(e) was repeated except that there was used instead of wool fibers a power of a porous swollen matter which was obtained by heating wool in an autoclave by means of saturated steam of 6 kg/cm$^2$ for 6 minutes and that 16.5 g of 2-acrylamido-2-methylpropanesulfonic acid was used instead of maleic acid, thereby obtaining 4.5 g of keratin-S-(2-acrylamido-2-methylpropanesulfonic acid).

EXAMPLE 1

Shampoo compositions containing 30% of coconut fatty acid diethanolamide and suitable amounts of perfumes, and anionic active agents and decomposition derivatives of keratin materials indicated in Table 1 were prepared to conduct their performance evaluation tests. The results are shown in Table 2.

The evaluation tests were conducted according to the following methods.

(1) Lathering test

To an aqueous 1% solution of each shampoo composition was added an artificial stain of 0.1% of lanolin, which was agitated in a cylinder by means of a plain propeller at a rate of 1000 r.p.m. at 40° C. for 5 minutes under such conditions that the rotation was reversed every 10 seconds. Thirty seconds after completion of the agitation, the amount of lather was measured.

(2) Feeling of Lather

After thirty grams of a human hair had been wetted with water at 40° C., the excess water was squeezed out to permit 20 g of the water to be contained. Then, the hair was washed by use of 1 g of each shampoo composition and the feeling of the lather was sensorially evaluated by a pannel of twenty female members.

Evaluation Items

The degree of easiness of passing fingers through hair while washing was evaluated as "slipping of lather" and the appearance of the lather was evaluated from a viewpoint of "creaminess".

Evaluation Standards

*The slipping of lather is better than that of reference product or the appearance of lather is more creamy.
*Equal to reference product.

| Reference Product: | |
|---|---|
| Sodium polyoxyethylene (3) laurylsulfate | 15% |
| Coconut fatty acid diethanolamide | 3 |
| Perfume | suitable amount |
| Water | balance (pH 7.2) |

(3) Combing Force

After thirty grams of an artificial hair was wetted with water at 40° C., the excess water was squeezed out to permit 20 g of water to be contained. One gram of each shampoo composition was used for washing of the hair and a rinsing operation was repeated twice. The hair was attached to a strain gauge after the excess water was squeezed out and combed to measure a force exerted on the hair at the time of the combing (wet state). Then, the hair was dried by a dryer and allowed to stand overnight in an air-conditioned room of 20° C. and 65% R.H. and then attached to a strain gauge, followed by combing to measure a force exerted on the hair at the time of combing (dry state).

(4) Hair Fly

On the measurement of the "combing force" in the dry state, it was observed whether or not the hair fly phenomenon occurred by the action of static electricity.

Evaluation

*Hair fly took place.
*Hair fly did not take place.

TABLE 1

| Sample No. | Anionic Surface Active Agent | Decomposition Derivative of Keratin Material |
|---|---|---|
| 1 | triethanolamine lauryl sulfate (15%) | Decomposition derivative of reference 1-(a) (2%) |
| 2 | triethanolamine lauryl sulfate (15%) | Decomposition derivative of reference 1-(b) (2%) |
| 3 | triethanolamine lauryl sulfate (15%) | Decomposition derivative of reference 2-(a) (2%) |
| 4 | triethanolamine lauryl sulfate (15%) | Decomposition derivative of reference 2-(b) (2%) |
| 5 | triethanolamine lauryl sulfate (15%) | Decomposition derivative of reference 2-(c) (2%) |
| 6 | triethanolamine lauryl sulfate (15%) | Decomposition derivative of reference 2-(d) (2%) |
| 7 | triethanolamine lauryl sulfate (15%) | Decomposition derivative of reference 2-(e) (2%) |
| 8 | triethanolamine lauryl sulfate (15%) | Decomposition derivative of reference 2-(f) (2%) |
| 9 | sodium lauryl sulfate (15%) | Decomposition derivative of reference 1-(a) (2%) |
| 10 | sodium polyoxyethylene (2) lauryl sulfate (15%) | Decomposition derivative of reference 1-(a) (2%) |
| 11 | ammonium lauryl sulfate (15%) | Decomposition derivative of reference 1-(a) (2%) |
| 12 | sodium lauryl sulfate (15%) | Decomposition derivative of reference 1-(a) (0.1%) |
| 13 | sodium lauryl sulfate (15%) | Decomposition derivative of reference 1-(a) (0.5%) |
| 14 | sodium lauryl sulfate (15%) | Decomposition derivative of reference 1-(a) (10%) |
| 15 | sodium lauryl sulfate (15%) | Decomposition derivative of reference 1-(a) (20%) |
| 16 | sodium polyoxyethylene (2) lauryl sulfate (15%) | Decomposition derivative of reference 2-(a) (0.1%) |
| 17 | sodium polyoxyethylene (2) lauryl sulfate (15%) | Decomposition derivative of reference 2-(a) (1.0%) |
| 18 | sodium polyoxyethylene (2) lauryl sulfate (15%) | Decomposition derivative of reference 2-(a) (10%) |
| 19 | sodium polyoxyethylene (2) lauryl sulfate (15%) | Decomposition derivative of reference 2-(a) (20%) |
| 20 | triethanolamine lauryl sulfate (15%) | acid decomposition product of collagen (M.W. 10,000–20,000) (2%) |
| 21 | triethanolamine lauryl sulfate (15%) | alkali decomposition product of collagen (M.W. 800–1,000) (3%) |
| 22 | triethanolamine lauryl sulfate (15%) | nil |

TABLE 2

| | Lathering Characteristics | | | Characteristics after Washing | | |
|---|---|---|---|---|---|---|
| | Amount | Felling of Lather | | Combing force (g) | | |
| Sample No. | of lather (ml) | Slipping of lather | Creaminess | Wet st. | Dry st. | Hair fly |
| 1 | 170 | o | o | 200 | 80 | o |
| 2 | 168 | o | o | 195 | 85 | o |
| 3 | 170 | o | o | 190 | 80 | o |
| 4 | 165 | o | o | 180 | 75 | o |
| 5 | 160 | o | o | 220 | 90 | o |
| 6 | 165 | o | o | 205 | 90 | o |
| 7 | 167 | o | o | 200 | 85 | o |
| 8 | 165 | o | o | 205 | 85 | o |
| 9 | 165 | o | o | 180 | 80 | o |
| 10 | 165 | o | o | 205 | 85 | o |
| 11 | 174 | o | o | 190 | 80 | o |
| 12 | 142 | o~Δ | o~Δ | 320 | 160 | o~Δ |
| 13 | 154 | o | o | 210 | 105 | o |
| 14 | 166 | o | o | 205 | 85 | o |
| 15 | 170 | o | o | 200 | 85 | o |
| 16 | 135 | o~Δ | o~Δ | 295 | 160 | o~Δ |
| 17 | 151 | o | o | 220 | 110 | o |
| 18 | 162 | o | o | 195 | 95 | o |
| 19 | 159 | o | o | 200 | 95 | o |
| 20 | 152 | Δ | Δ | 350 | 175 | Δ |
| 21 | 148 | Δ | Δ | 360 | 170 | Δ |
| 22 | 112 | x | x | 470 | 210 | x |

EXAMPLE 2

Shampoo compositions A (inventive product) and B (comparative product) of the following formulations were prepared and their effects were evaluated by a paired sensorial evaluation by a panel of 20 female members. The results are shown in Table 3.

| Shampoo composition: | A | B |
|---|---|---|
| Triethanolamine lauryl sulfate | 18.0 (%) | 18.0 (%) |
| Decomposition derivative of keratin material (obtained in reference 2-(a)) | 2.0 | — |
| Perfume | 0.3 | 0.3 |
| Colorant | Small amount | Small amount |
| Water | Balance | Balance |

TABLE 3

| Evaluation Item | Shampoo A being better | Shampoo B being better | Hard to say |
|---|---|---|---|
| creaminess of lather | 15 | 3 | 2 |
| easiness of passing fingers through hair | 17 | 1 | 2 |
| feel of hair after washing (wet) | 17 | 0 | 3 |
| feel of hair after washing (dry) | 19 | 0 | 1 |
| easiness of setting hair together | 18 | 0 | 2 |

EXAMPLE 3

The shampoo composition A (inventive product) used in Example 2 and a commercially available shampoo were used to check the degree of irritation to eyes by the Oraize method. That is, 0.1 ml of each shampoo composition was dropped in the eyes of five healthy white, male rabbits weighing 2.5–3.0 kg. Three hours and 24 hours after the dropping, the cornea, iris and conjuctiva of five rabbits were observed and the results were calculated according to the following inspection method to give average values. A total value was obtained by adding a value which was obtained by multiplying two average values of cornea by themselves and further by 5, a value which was obtained by multiplying an average value of the iris by 5, and a value which was obtained by adding three average values of the conjuctiva to one another and then multiplied by 2. A higher total value shows a greater degree of irritation to eyes. The results are shown in Table 4.

| Inspection Method: | | | |
|---|---|---|---|
| 1. | Cornea: | Opacity | 0~4 |
| | | Area of cornea involved | 0~4 |
| 2. | Iris: | Congestion | 0~2 |
| 3. | Conjuctiva: | Redness | 0~3 |
| | | Chemosis | 0~4 |

TABLE 4

| Shampoo Composition | | A (Inventive product) | | Commercially available product | |
| --- | --- | --- | --- | --- | --- |
| Time after dropping (hrs.) | | 3 | 24 | 3 | 24 |
| Cornea | Opacity | 1 | 0 | 1 | 1 |
| | Area of cornea involved | 1 | 0 | 4 | 2 |
| Iris | Congestion | 0 | 0 | 0 | 0 |
| Conjuc- | Redness | 1 | 0 | 2 | 1 |
| tiva | Chemosis | 0 | 0 | 2 | 1 |
| | Discharge | 1 | 0 | 2 | 1 |
| | Total | 9 | 0 | 32 | 16 |

What is claimed is:

1. A shampoo composition comprising a shampoo base containing at least one anionic surface active agent in an amount of 5–30% by weight of said shampoo composition and an oxidation or reduction decomposition derivative of keratin material in an amount of from 0.05–10% by weight having a thiol group selected from the group consisting of

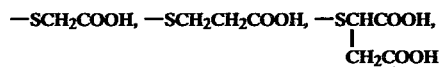

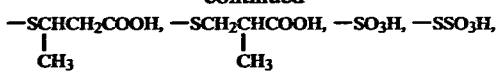

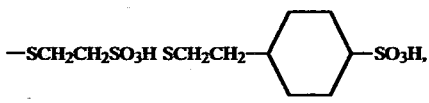

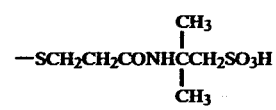

SCH$_2$CH$_2$SO$_2$CH$_2$COOH and a mixture thereof.

2. A shampoo composition according to claim 1, wherein said at least one anionic surface active agent is contained in an amount of 10 to 25% by weight of said shampoo composition.

3. A shampoo composition according to claim 1, wherein the amount of said decomposition derivative of keratin material is in the range of 0.2 to 3% by weight.

4. A shampoo composition according to claim 1, wherein said shampoo composition is adjusted to have a pH range of 4–8.

5. A shampoo composition according to claim 1, wherein said at least one anionic surface active agent is a linear or branched alkylsulfate having 10 to 16 carbon atoms on average, a polyoxyethylenealkylsulfate whose alkyl group has 8 to 20 carbon atoms on average, or an olefinsulfonate having 10 to 20 carbon atoms on average.